United States Patent [19]

Straford et al.

[11] Patent Number: 5,591,882

[45] Date of Patent: Jan. 7, 1997

[54] PROCESS FOR PREPARING ORGANOPHOSPHATES USEFUL FOR INCREASING THE OCULAR HAEMO- AND BIOCOMPATIBILITY OF SYNTHETIC POLYMERS

[75] Inventors: Peter W. Straford; Michael J. Driver, both of Uxbridge, United Kingdom

[73] Assignee: Biocompatibles Limited, Uxbridge Middlesex, United Kingdom

[21] Appl. No.: 423,983

[22] Filed: Apr. 18, 1995

Related U.S. Application Data

[62] Division of Ser. No. 927,293, filed as PCT/GB91/00338, Mar. 5, 1990, Pat. No. 5,422,402.

[30] Foreign Application Priority Data

Mar. 5, 1990 [GB] United Kingdom ............ 9004881

[51] Int. Cl.$^6$ ................................ C07H 9/09
[52] U.S. Cl. ................. 558/87; 558/83; 558/169
[58] Field of Search ................... 558/169, 87

[56] References Cited

U.S. PATENT DOCUMENTS

| | | | |
|---|---|---|---|
| 4,492,659 | 1/1985 | Bosies et al. | 558/169 |
| 4,647,685 | 3/1987 | Bonjouklian et al. | 558/169 |
| 4,721,800 | 1/1988 | Chapman . | |
| 5,064,961 | 11/1991 | Bisacchi et al. | 544/276 |

FOREIGN PATENT DOCUMENTS

| | | |
|---|---|---|
| 0157469 | 10/1985 | European Pat. Off. . |
| 0332129 | 9/1989 | European Pat. Off. . |
| 3109141 | 9/1982 | Germany . |

OTHER PUBLICATIONS

Greene, T. W.; *Protective Groups in Organic Synthesis*; John Wiley & Sons: New York, 1981; pp. 44–46.

*Primary Examiner*—Johann Richter
*Assistant Examiner*—Michael G. Ambrose
*Attorney, Agent, or Firm*—Sughrue, Mion, Zinn, Macpeak & Seas

[57] ABSTRACT

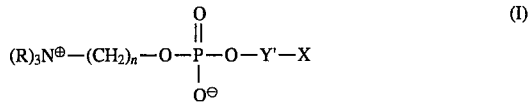

A process for treating suitable synthetic polymers comprising the steps of (a) where appropriate, activating the surface to be treated, and, if necessary, providing spacer groups thereon; and (b) treating the surface with a compound of formula (I), wherein Y' is an alkylene group optionally containing an aryl group, a poly(ethylene glycol) or a glycerol group; R may be the same or different and each is a straight or branched $C_{1-4}$ alkyl group, n is from 1 to 4 and X is a group which reacts with functional groups of the polymer. Polymeric surfaces and materials thus produced and shaped articles containing such surfaces and materials.

10 Claims, No Drawings

PROCESS FOR PREPARING ORGANOPHOSPHATES USEFUL FOR INCREASING THE OCULAR HAEMO- AND BIOCOMPATIBILITY OF SYNTHETIC POLYMERS

This is a divisional of application Ser. No. 07/927,293 filed Sep. 23, 1992, now U.S. Pat. No. 5,422,402, which was filed under 35 U.S.C. 371 and was based upon PCT International Application No. PCT/GB91/00338, filed on Mar. 5, 1991.

The present invention relates to the treatment of synthetic polymers to improve their ocular, haemo and biocompatibility and to polymeric materials having a surface thus treated.

Synthetic polymers are widely employed in a variety of biological applications such as hard, soft and intraocular lenses, blood contact and blood filtration applications and in biological separation systems. However, it is widely recognised that the performance of synthetic polymers in biological systems can be compromised by the adsorption of proteins and cells at polymer surfaces. This can result in a variety of problems such as reduction of the gas permeability and patient discomfort with polymeric lens devices, the activation of intrinsic and extrinsic blood clotting pathways in blood contacting materials and a reduction in specificity, as a result of non-specific protein deposition and fouling, in separation systems.

The present invention relates to synthetic polymer coating treatments which are simple and employ economical and readily available materials. The coating produced is permanent and results in reduced protein and cell deposition at polymer surfaces.

The invention therefore provides a process for treating suitable synthetic polymers comprising the steps of a) where appropriate, activating the surface to be treated, and, if necessary, providing spacer groups thereon; and b) treating the surface with a compound of formula (I):

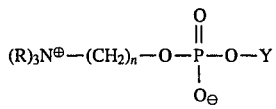
(I)

where Y is -(CH$_2$)$_p$ X, -(CH$_2$)$_a$-Ar-(CH$_2$)$_b$X, -(CH$_2$CH$_2$O)$_c$ X or

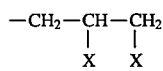

wherein the groups R may be the same or different and each is a straight or branched C$_{1-4}$ alkyl group, n is from 1 to 4 p is from 1 to 30, preferably 1 to 22, for instance 1 to 6,

Ar is a para- or meta-disubstituted aryl or heteroaryl group, a and b are the same or different and each is from 0 to 5, and a+b is from 1 to 10;

c is from 1 to 20, preferably 1 to 8; and

X is a group which reacts with fuctional groups on the polymer, with the proviso that when Y is -(CH$_2$)$_p$X or -(CH$_2$CH$_2$O)$_c$X and c is 1, then X is:

an epoxide group;

a group

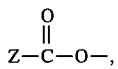

where Z is C$_{1-4}$ straight or branched alkyl optionally substituted with one or more electron withdrawing groups or Z is an optionally substituted aromatic or heteroarmoatic ring system;

a group

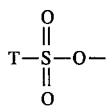

where T is a straight chain alkyl of 1 to 4 carbon atoms optionally substituted by alkyl or alkoxy of 1 to 4 carbon atoms or halogen or an optionally substituted aromatic or heteroaromatic ring system;

a group

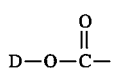

where D is an optionally substituted aromatic or heteroaromatic ring system or an N- substituted imide derivative;

a group

where E is a halogen atom, or an N- substituted nitrogen-containing heteroaromatic ring system; or a group of formula

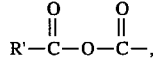

were R is a group

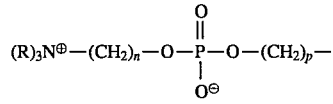

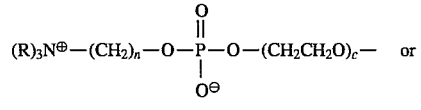 or

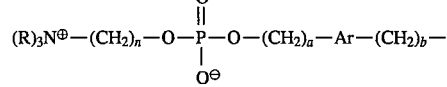

where R, n, a, b, c, and p are as hereinbefore defined, or R' is an alkyl group, optionally substituted by alkyl or alkoxy of 1 to 4 carbon atoms or halogen or is an optionally substituted aromatic or heteroaromatic ring system.

Preferably R is methyl, ethyl, n-propyl or n-butyl. Preferably all R groups are the same and most preferably all R groups are methyl.

Where Y is a group of formula -(CH$_2$)$_a$-Ar-(CH$_2$)$_b$X preferably Ar is an aromatic group which comprises one aromatic ring or two fused aromatic rings, eg. a phenyl or naphthyl group, which is optionally further substituted by alkyl or alkoxy of 1 to 4 carbon atoms, halogen, nitro, amino or mono- or dialkylamino wherein the alkyl substituents each contain 1 to 4 carbon atoms, or Ar is a heteroaromatic group which comprises a five, six or seven membered heteroaromatic ring, optionally fused with a further five, six or seven membered aromatic or heteroaromatic ring, which ring or rings contain from one to three oxygen, nitrogen or sulphur atoms and are optionally further substituted by alkyl or alkoxy of 1 to 4 carbon atoms, halogen, nitro, amino or mono- or dialkylamino wherein the alkyl substituents each contain 1 to 4 carbon atoms.

Where Y is a group of formula $-(CH_2)_a\text{-}Ar\text{-}(CH_2)_bX$ preferably a is 1, b is 1 or both a and b are greater than or equal to 1.

Suitable values for X include epoxides for example

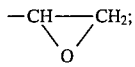

a group

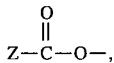

where Z is a $C_{1-4}$ straight or branched alkyl group optionally substituted with one or more electron withdrawing groups (e.g. halo, nitro or cyano) or Z is an optionally substituted aromatic ring system, for example p-nitrophenyl or, an optionally substituted heteroaromatic ring system, for example imidazole, a group

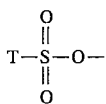

where T is a straight chain alkyl of 1 to 4 carbon atoms, optionally substituted by alkyl or alkoxy of 1 to 4 carbon atoms or halogen, or is an optionally substituted aromatic or heteroarmoatic ring system;

a group

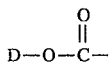

where D is an optionally substituted aromatic or heteroaromatic ring system or an N-substituted imide derivative, for example succinimide;

a group

where E is a halogen atom, and N- substituted nitrogen-containing heteroaromatic ring system, for example imidazole, or a group of formula

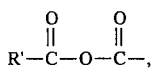

where R' is

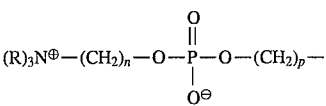

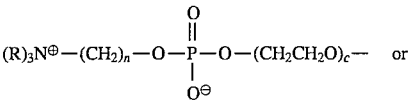

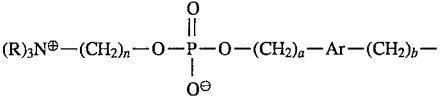

where R, n, a, b, c, and p are as hereinbefore defined, or R' is an alkyl group, optionally substituted by alkyl or alkoxy of 1 to 4 carbon atoms or halogen or is an optionally substituted aromatic or heteroaromatic ring system.

Preferably the aforesaid aromatic ring systems comprise one, or two fused, aromatic rings (eg a phenyl or naphthyl group) which are unsubstituted or substituted by alkyl or alkoxy of 1 to 4 carbon atoms, halogen, nitro, amino or mono- or dialkylamino wherein the alkyl substituents contain 1 to 4 carbon atoms.

Preferably the aforesaid heteroaromatic ring systems, except as otherwise required, comprise a five, six, or seven membered heteroaromatic group, optionally fused with a further five, six or seven membered aromatic or heteroaromatic ring which rings contain from 1 to 3 oxygen, nitrogen or sulphur atoms and are unsubstituted or substituted by alkyl or alkoxy of 1 to 4 carbon atoms, halogen, nitro, amino or mono- or dialkylamino wherein the alkyl substituents contain 1 to 4 carbon atoms.

The preferred compounds of formula (I) are 2-[{2-(1-imidazolecarbonyloxyethoxy)hydroxyphosphinyl}oxy]-N,N,N-trimethylethanaminium hydroxide, inner salt, 2-[{4-(1-imidazolecarbonyloxybutoxy)hydroxyposphinyl}oxy]-N,N,N-trimethylethanaminium hydroxide, inner salt and 1,2-bis-O-imidazolecarbonyl-sn-glycero-3-phosphorylcholine.

In the process of the invention, step (a) may be omitted where the polymer surface has sufficient free hydroxyl, carboxyl or primary and secondary amino groups for reaction with compounds with formula (I).

Typical of such polymers having adequate surface free reactive groups are those synthesised from hydroxyalkyl acrylates/methacrylates, (hydroxyl groups), acrylic and methacrylic acids (carboxyl groups), aminoalkylacrylates, aminoalkylmethacrylates, polyurethanes having amino group-containing substituents, polysaccharides, cellulose and modified celluloses.

For other synthetic polymers which do not have adequate free surface hydroxyl, carboxyl or amino groups, such as poly(methylmethacrylate) (PMMA), polypropylenes and polyethylenes, it is necessary to activate the surface before treatment with the compounds of formula (I). This can be achieved by known surface etching and derivatisation techniques, such as grafting, which introduce carboxyl, hydroxyl or primary or secondary amino groups on surfaces (see Chemical reactions of polymers, Ed E Fettes, 1964 Interscience Publishers, London).

It may be necessary or desirable and can be advantageous to provide spacer groups between the surface and the residues of the compound of formula (I). Typically such spacer groups are derived from straight chain alkanes bearing terminal reactive groups such as hydroxyl, carboxyl or, preferably, amino groups, for instance, α,ω-diamino alkanes such as 1,12-diamino dodecane. The spacer groups are introduced by reaction with active hydroxyl, carboxyl or primary or secondary amino groups on the polymer surface; if not normally present on the polymer surface these groups may be introduced by the activation methods described above. The compound of formula (I) is then reacted with the free reactive group on the residue of the spacer compound. Spacer compounds are widely available or may be produced by conventional methods well known in the art of organic chemistry. Reaction of spacer compounds with (activated) polymer surfaces is achieved by well known synthetic methods. The residues of the spacer groups are reacted with compounds of formula (I) as described below for the reaction with (activated) polymer surfaces.

Step (b), the treatment process is suitably conducted in an aqueous medium at neutral, slightly acidic, acid or alkaline pH in the range from pH 3 to 13 for instance 5 to 12. Preferably the reaction is conducted in the presence of a base such as sodium hydroxide at low concentrations, for instance at 0.2M or less. Most preferably the pH of the medium employed is adjusted and controlled using buffers such as sodium bicarbonate at pH 8 to 10 for instance 8 to 9 or the pH is adjusted during the process using appropriate acid or base to produce optimum reactions conditions.

The coating reaction is preferably conducted at any temperature from above 0° C. provided that the temperature does not damage the chemical structure or physical properties of the material being treated for instance from slightly below to slightly above ambient temperature. Preferably the reaction is conducted at up to 50° C., more preferably at from 4° C. to 40° C.

Prior to the treatment process the material is preferably equilibrated in the medium to be used as the solvent for the treatment. The time for the equilibration step is 15 mins to 3 hours, preferably 30 mins to 1 hour.

The coating reaction is conducted in a solution of a compound of formula (I) at a suitable concentration, for instance from 0.01M to 2M, preferably 0.25M to 1M. the time of reaction is typically from 30 mins to 24 hours, preferably 8 hours to 16 hours.

Following treatment, the materials may be washed to removed unreacted compound and side-products for instance using borate buffered saline or another physiologically acceptable buffer. The coating is sufficiently robust that coated polymers may be sterilised, for instance by autoclaving.

In certain biological applications of synthetic polymers, such as soft contact lenses and separation systems support polymers, it is sometimes necessary to maintain an optimal level of water at the surface of and within the polymer in order for the device or material to function at an optimal level of performance.

Where appropriate the water content of the material may also be affected by the treatment. By judicious choice of the treatment concentration the required water content can be achieved.

Polymeric surface treatments of the invention provide for physically and chemically stable products which are durable.

When the compound of formula (I) is an imidazole derivative of a hydroxyphosphoryl choline the reaction with a surface bearing hydroxyl group generates a carbonate linkage:

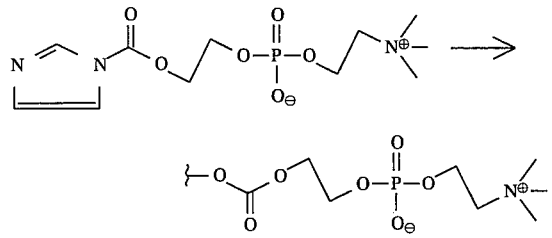

Similarly, reactions with surfaces bearing carboxyl or amino groups may lead to the formation of ester or carbamate linkages respectively.

When the compound of formula (I) is a sulphonate ester phosphoryl choline derivative reaction with polymeric hydroxyl groups generates and ether linkage;

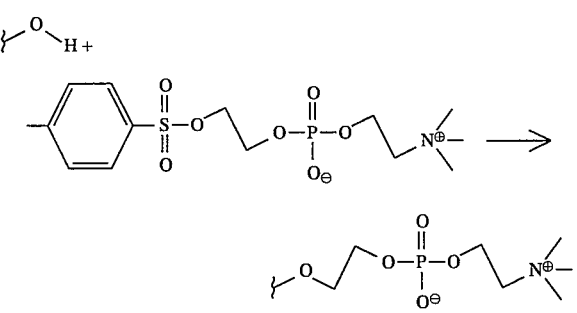

A compound of formula (I) which contains an epoxide functionality reacts with surfaces bearing hydroxy groups to give hydroxy ethers

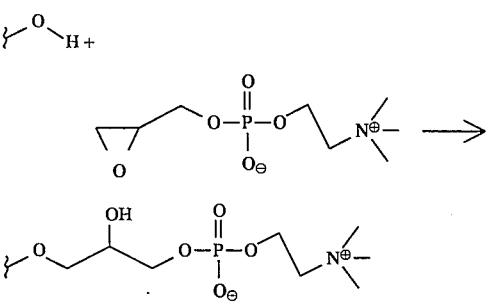

A compound of formula (I) which is an acid imidazolide phosphoryl choline derivative reacts with surfaces bearing hydroxyl groups to give esters.

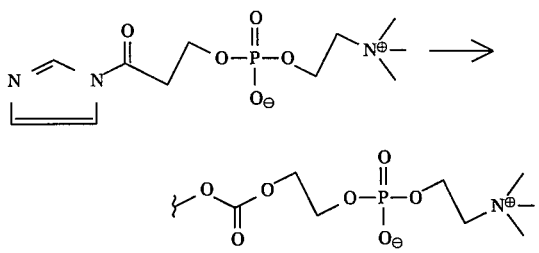

and with surfaces bearing amino groups to give amides.

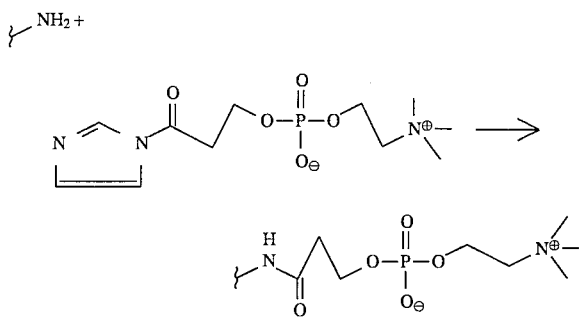

The present invention further provides polymeric surfaces coated or derivatised with covalently bound residues of a compound of formula (I).

The invention also provides a polymeric material having a surface coated or derivatised with covalently bound residues of a compound of formula (I).

The invention also further provides shaped articles having such a polymeric surface or comprising such polymeric material.

The compounds of formula (I) may be produced from known methods using readily available reagents, They may be produced from phosphoryl choline derivatives.

Compounds of formula (I) wherein X is an epoxide may be prepared by reaction of an unsaturated phosphoryl choline derivative of formula (II) in which R, n and Y are as hereinbefore defined, with an epoxidising reagent, for example m-chloroperbenzoic acid, as shown in Scheme 1 hereinafter.

The epoxidation may be performed using conventional reaction conditions. The unsaturated phosphoryl choline derivatives of formula (II) may be prepared using the method disclosed in JP-A-184093/85.

Alternatively compounds of formula (I) in which X is an epoxide may be prepared by the reaction of a salt of formula (III) in which R, n and Y are as hereinbefore defined, e.g. a silver salt, with a haloepoxide, e.g. a bomo- or chloro-epoxide, for instance epichlorohydrin or epibromohydrin as shown in scheme 2 hereinafter.

The reaction is typically performed in an organic anhydrous aprotic solvent such as dimethyl sulphoxide, at a temperature from −10° to 40° C., for instance at about 0° C. The salts of formula (III) may be prepared by known methods.

Compounds of formula (I) wherein X is a group ZC(O)O- and Z is an unsubstituted or substituted imidazolide may be obtained by treatment of a hydroxyphosphoryl choline derivative of formula (IV) in which R, n and Y are as hereinbefore defined with 1,1'-carbonyldiimidazole (CDI) or a substituted derivative thereof as shown in Scheme 3 hereinafter.

The hydroxy phosphorylcholine derivative of formula (IV) may be reacted with 1,1'-carbonyldiimidazole or a substituted derivative thereof, optionally in the presence of a tertiary organic base, for example triethylamine under anhydrous conditions to give the desired imidazole phosphorylcholine derivative. An excess of 1,1'-carbonyldiimidazole may be used, for instance 1.1 to 5 equivalents, preferably 1.4 to 2 equivalents, optionally with 1.1 to 5 equivalents of tertiary organic base, preferably 1.5 to 2 equivalents. The reaction may be conveniently performed in a suitable anhydrous, aprotic solvent, for example dimethyl sulphoxide or dimethylformamide. The reaction is typically performed at from 0° to 50° C., preferably about 21° C.

under an inert atmosphere, for example, nitrogen and, for 0.25 to 6 hours, preferably 0.5 to 1 hour. The required product is conveniently isolated by precipitation from the reaction mixture using a suitable solvent, for example dry acetone.

Other compounds of formula (I) in which X is a group ZC(O)O- may be obtained by the reaction of a hydroxyphosphorylcholine derivative of formula (IV) with an acid of formula ZCOOH or a reactive derivative thereof, such as an acid halide, acid anhydride, or ester, using conventional conditions.

The hydroxy phosphorylcholine derivatives of formula (IV) may be prepared as outlined in Scheme 4 hereinafter or by direct analogy thereof. A suitable diol, ethylene glycol for example, is monoprotected using a protecting agent, such as a silylating agent, tert-butyl-dimethylsilyl chloride (TBDMS-Cl) for example and the coupled to 2-chloro-2-oxo-1,3,2-dioxaphospholane in the presence of either an inorganic or an organic base, triethylamine for example. Both the preceding reactions are conveniently performed in an inert organic solvent such as dichloro-methane or diethyl ether. The coupling reaction is typically performed at a temperature of about −20° C. and for about 2 hours. The coupled product is then heated in a sealed vessel with an excess of anhydrous tertiary amine, for instance trimethylamine, (using from 1.1 to 5 equivalents) in an inert solvent for example acetonitrile, at 40° to 80° C., eg. about 55° C., preferably 60° to 70° C., for 1 to 5 days, preferably 2, or more preferably 3 days. The protected hydroxyphosphorylcholine derivative is then deprotected using suitable conditions, for example hydrogen fluoride pyridine complex in dry tetrahydrofuran and dry methanol at a temperature typically from −20° to 40° C., preferably about 21° C. for 1 to 24 hours, preferably 10 to 16 hours. The compound of formula (IV) produced may be purified using medium pressure chromatography on a suitable support silica-gel for example, eluting with a suitable mixture of ethyl acetate and methanol.

As an alternative to a silyl protecting group, other known alcohol protecting groups may be used in a conventional manner. For instance a vinyl ether protecting group, eg. ethyl vinyl ether may be used. The starting diol may be protected with such a group by reaction in the presence of an acid such as p-toluene sulphonic acid at a temperature of about 0° C. over a period of about 2 hours. The product thus obtained may be purified by distillation at atmospheric pressure. After coupling with the oxaphospholane and ring opening using the method described above, the de-protection may be accomplished using acid, e.g. dilute HCl, at a temperature of about 0° C.

Compounds of formula (I) wherein X is a group

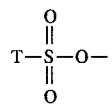

may be obtained by treatment of a hydroxy phosphoryl choline derivative of formula (IV) with a sulphonyl halide e.g. chloride derivative in the presence of a tertiary organic base for instance triethylamine. Scheme 5 below illustrates such a reaction using toluenesulphonyl chloride.

The reaction is conveniently performed in an anhydrous aprotic solvent, dimethylsulphoxide for example, at ambient temperature, preferably about 21° C. using an excess of sulphonyl chloride (1.1 to 5 equivalents, preferably 1.5 to 2 equivalents) and an excess of base (1.1 to 5 equivalents, preferably 1.5 to 2 equivalents).

Compounds of formula (I) wherein X is an activated acid derivative are obtained from reaction of a suitable carboxylphosphorylcholine derivative of formula (V)

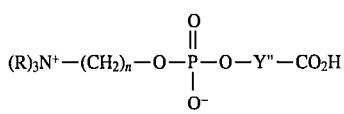  (V)

in which R, and n are as hereinbefore defined and Y" is a group -(CH$_2$)$_p$-, -(CH$_2$)$_a$-Ar-(CH$_2$)$_b$-, -(CH$_2$CH$_2$O)$_c$- or

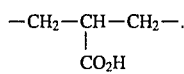

Esters, where X is a group

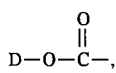

for example, may be obtained via carbodiimide mediated coupling with a suitable heteroaromatic alcohol, a phenol or an N-hydroxy-derivative, as illustrated for the case of succinimide by Scheme 6. A compound where X is EC(O), and E is a substituted or unsubstituted imidazole may be obtained by reaction of a carboxy phosphorylcholine derivative of formula (V) with 1,1'-carbonyldiimidazole, or a substituted derivative thereof as illustrated in Scheme 7. Other compounds where X is EC(O) may be obtained by analogous routes or by conventional routes for the formation of acid halides (where E is halogen). Compounds of formula (I) where X is a group R'CO$_2$CO-, may be obtained by reaction of a carboxyphosphorylcholine derivative of formula (V) with a chloroformate or carboxylic acid or reactive derivative thereof such as an acid halide, ester, or acid anhydride. Phosphoric or sulphonic acids or derivatives thereof may be used to give suitable mixed anhydrides. These reactions may all be performed using conventional techniques and conditions.

The carboxyphosphoryl choline derivatives of formula (V) may be obtained by reaction of a suitable hydroxy ester with 2-chloro-2-oxo-1,3,2-dioxaphospholane in the presence of a suitable base. The dioxaphospholane ring is then opened using, for example trimethylamine, and the ester group hydrolysed under conventional conditions to given the required acid derivative. The procedure is analogous to that illustrated in Scheme 4 for the preparation of compounds of formula (IV). The conditions described above in relation to the coupling reaction with the dioxaphospholane and subsequent ring-opening are typically employed.

Compounds of formula (I) in which Y is a glycerol residue, -CH$_2$CH(X)CH$_2$X, may be obtained by treatment of glycerophosphoryl choline with a suitable reagent such that a compound with the desired value for X is isolated. For example, reaction of glycerophosporyl choline, cadmium chloride complex in an aprotic solvent, for example dimethyl sulphoxide, for example with a suitable base, for example, triethylamine and 1,1'-carbonyldiimidazole gives a 1,2-bisimidazole derivative as shown in Scheme 8.

SCHEMES 1 TO 8

In scheme 1 to 3, Y' is a group -(CH$_2$)$_p$-, -(CH$_2$)$_a$-Ar-(CH$_2$)$_b$-, -(CH$_2$CH$_2$O)$_c$-, or

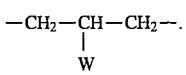

where W is

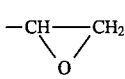

in Schemes 1 and 2 and

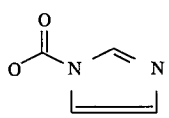

in Scheme 3.

SCHEME 1

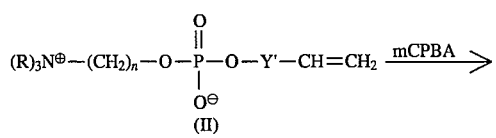

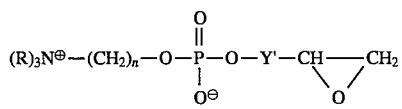

SCHEME 2

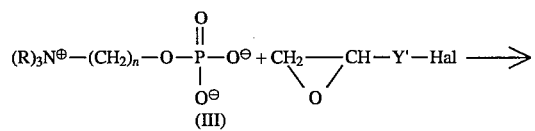

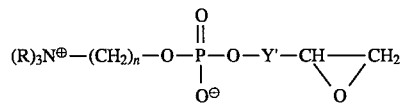

SCHEME 3

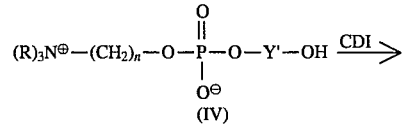

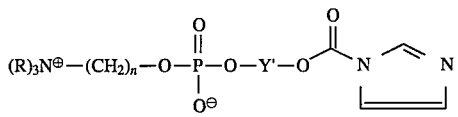

SCHEME 4

HOCH$_2$CH$_2$OH + t-butyldimethylsilyl chloride

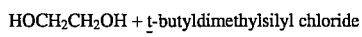
base

11
-continued
SCHEME 4

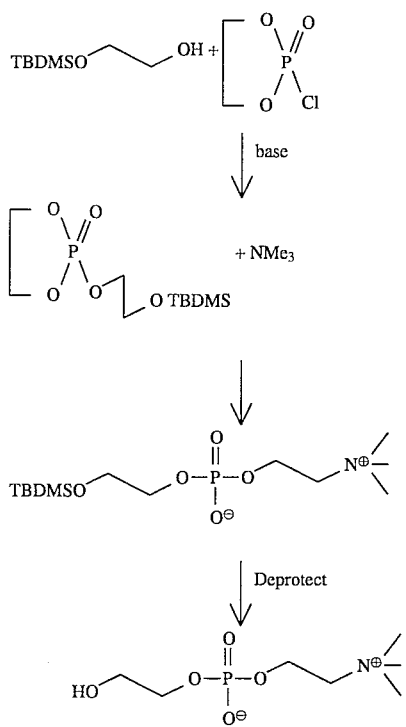

SCHEME 5

SCHEME 6

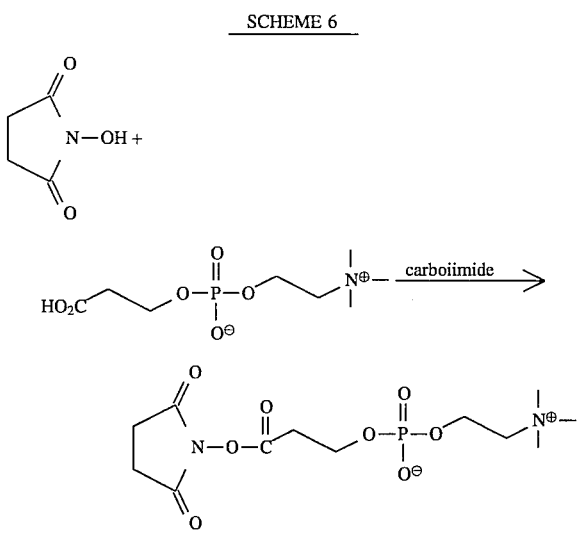

12
SCHEME 7

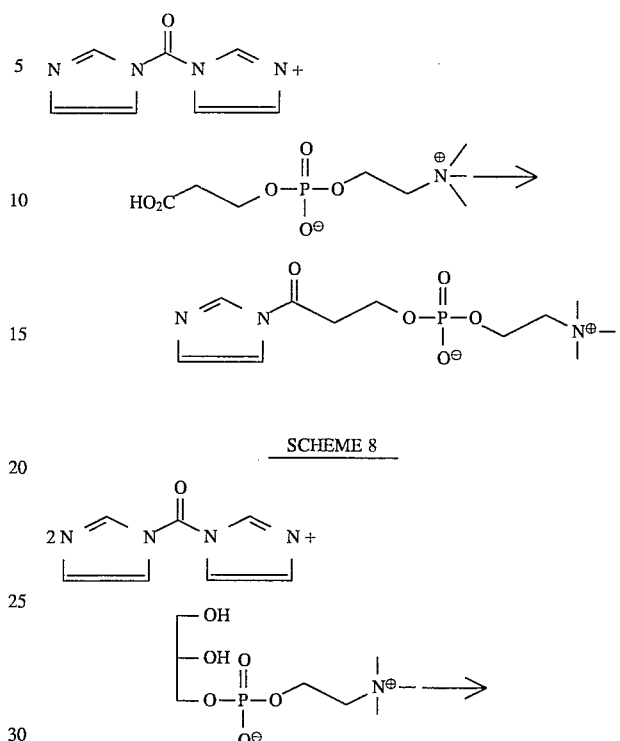

SCHEME 8

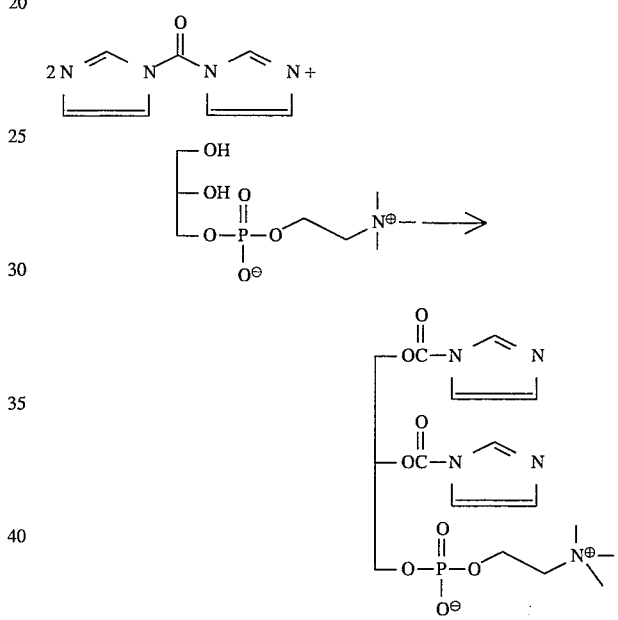

The preparation of 2-[{2-(hydroxyethoxy)hydroxyphosphinyl}oxy]-N,N,N-trimethylethanaminium hydroxide, inner salt has been described (Biomaterials, 1986, 121 and EP-A-157, 469). This technique may also be applied to prepare analogous compounds.

The invention will now be illustrated by the following examples which are not intended to limit the scope of protection in anyway:

EXAMPLE 1

A cellulose (Cupraphan) substrate having surface hydroxymethyl groups was activated by oxidation with chromic acid (Sodium dichromate, 1.25 g, dissolved in concentrated sulphuric acid, 25 cm$^3$, and diluted with water to 75 cm$^3$) for 3 minutes. The substrate is washed to remove acid. Spacer groups were then linked to the surface via the carboxyl groups produced by the chromic acid by reacting 1,12 dodecane diamine (0.7 g) and 1-(3-dimethylamino propyl)-3-ethylcarbodiimide hydrochloride (0.7 g) with the activated substrate in water (10 cm$^3$) at slightly acid pH (pH 5.6).

The activated surface bearing aminododecylamine spacer groups was reacted with 2-[{2-(1-Imidazolecarbonyloxyethoxy)hydroxyphosphinyl}oxy]-N,N,N-trimethylethanaminium hydroxide, inner salt, (0.3 g) in water (3 ml) at pH 9.5 (sodium bicarbonate) to give groups of formula

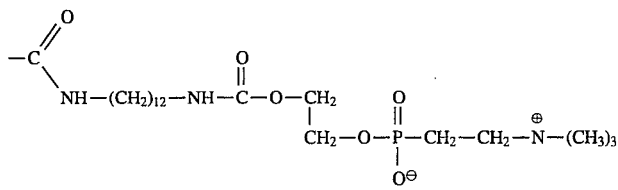

on the surface of the substrate.

PREPARATION EXAMPLE

Synthesis of 2-Chloro-2-oxo-1,3,2-dioxaphospholane

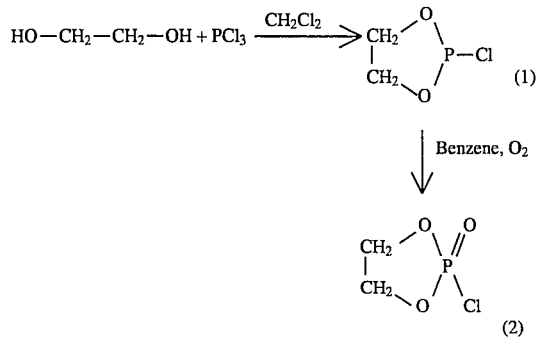

a) 2-Chloro-1,3,2-dioxaphospholane (1)

In a 3-necked 1L flask fitted with reflux condenser, drying trap, magnetic stirrer and pressure equalising dropping funnel was placed a solution of phosphorus trichloride (220 ml, 346.3 g, 2.52 mol) in methylene chloride (500 ml). Freshly dried and distilled ethylene glycol (139 ml, 154.7 g, 2.49 mol) was placed in the dropping funnel and added dropwise at such a rate that the evolution of hydrogen chloride did not become excessive. On completion of the addition, the flask was arranged for distillation and the solvent removed at atmospheric pressure. When the distillation temperature had reached 50° C., the apparatus was converted for vacuum distillation to give 2-chloro-1,3,2-dioxaphospholane as a colourless fuming liquid, bpt 57°–60° C./21 mmHg IR (vcm$^{-1}$, thin film) 2980, 2905, 1470, 1210, 1005, 930, 813, 770.

b) 2-Chloro-2-oxo-1,3,2-dioxaphospholane (2)

In a 1L flask fitted with a 3-necked adapter, magnetic stirrer, condenser and gas inlet tube, was placed a solution of the phospholane (1) (250 g, 1.98 mol) in dry benzene (600 ml). Dry oxygen was then passed through the stirred solution for 6 hrs. No attempt was made to regulate the temperature of the reaction. The solvent was removed by rotary evaporation and the residual liquid distilled to give 2-chloro-2-oxo-1,3,2-dioxaphospholane (164 g, 1.15 mol) as a colourless oil, bpt 95°–97° C./0.03 mmHg.

IR (vcm$^{-1}$, thin film) 2990, 2910, 1475, 1370, 1310, 1220, 1030, 930, 865, 830.

EXAMPLE 2

(2-(tert-Butyldimethylsilyloxy)ethanol

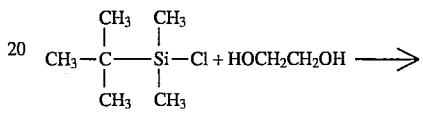

tert-Butyldimethylsilylchloride (100 g, 0.66M) in dry dichloromethane (70 ml) was added, drop-wise, to a stirred mixture of distilled ethylene glycol (205.6 g, 3.3M), dry dichloromethane (200 ml), triethylamine (120 ml, 0.86M) and 4-dimethylaminopyridine (8 g, 0.066M) at 0° C. under a nitrogen atmosphere. After the addition the mixture was allowed to warm to ambient temperature and was stirred for a further 3 hours. The mixture was then filtered and the filtrate washed with dilute sodium bicarbonate solution, brine, dried over magnesium sulphate, filtered and then evaporated in vacuo to give a pale yellow oil.

The oil was distilled to give the title compound as a colourless oil (bp 74°–76° C. 2 mm Hg).

$^1$HNMR (60 MH$_z$), (CDCl$_3$) 3.6 (4H,s), 2.4 (1H,s), 0.85 (9H,s) and 0.1 (6H,s) ppm.

2-(2-tert-Butyldimethylsilyloxyethoxy)-2-oxo-1,3,2-dioxaphospholane

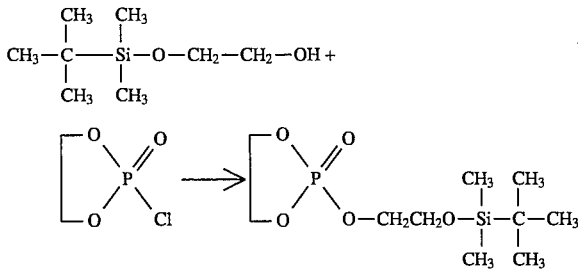

A solution of freshly prepared 2-chloro-2-oxo-1,3,2-dioxaphospholane (14.2 g, 0.1M) in dry dichloromethane (30 ml) was added, drop-wise, to a stirred mixture of 2-(tert-butyldimethylsilyloxy)ethanol (17.6 g, 0.1M), triethylamine (18.1 ml), 0.13M) in dry dichloromethane (30 ml) at 0° C. under a nitrogen atmosphere. The mixture was allowed to warm to ambient temperature and was stirred for a further 2 hours. The mixture was filtered and the filtrand washed with n-hexane. The filtrate was evaporated in vacuo, diluted with n-hexane (30 ml) filtered and the filtrate evaporated in vacuo to give a brown oil.

$^1$HNMR (60 MH$_z$) (CDCL$_3$) δ 4.6-3.6(8H, complex), 0.9 (9H,s) and 0.1 (6H, s) ppm.

2-[{2-(tert-Butyldimethylsilyloxyethoxy)hydroxyphosphinyl}oxy]-N,N,N-trimethylethanaminium hydroxide, inner salt

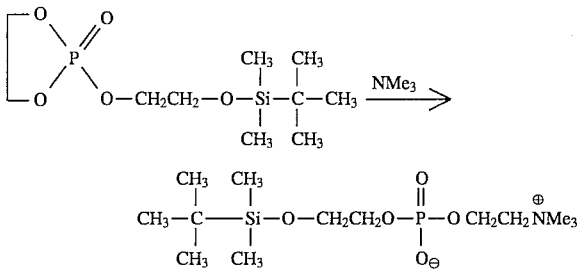

2-(2-tert-Butyldimethylsilyloxyethoxy)-2-oxo-1,3,2-dioxaphospholane (28 g, 0.1M) in dry acetonitrile (50 ml) was added to condensed trimethylamine (27 ml, 0.3M) in a pressure bottle. The vessel was sealed and warmed to 70° C. for 3 days. The mixture was allowed to cool and was stored at ambient temperature for 2 days. The crude reaction product was then dissovled in dry methanol (30 ml) and evaporated in vacuo to give the title compound $^1$HNMR (60 MH$_z$) (CD$_3$OD) 4.5-3.5 (8H, complex), 3.15 (9H,s), 0.9 (9H,s) and 0.05 (6H,s) ppm.

2-[{2-(Hydroxyethoxy)hydroxyphosphinyl}oxy]-N,N,N-trimethylethanaminium hydroxide, inner salt

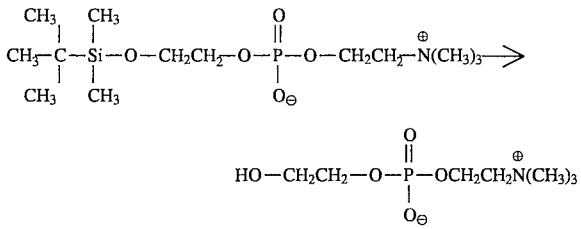

The protected hydroxyphosphorylcholine derivative (ca 0.1M) was dissolved in dry tetrahydrofuran (60 ml) and dry methanol (20 ml) and treated with hydrogen fluoride-pyridine complex (3.2 ml) at 0° C. under a nitrogen atmosphere. The mixture was stirred at ambient temperature overnight then poured into dry acetone (200 ml) and allowed to stand for 1 hour. The supernatant was decanted and the residue dissolved in methanol (40 ml) preadsorbed onto silica-gel and purified using column chromatography on silica gel eluting with ethyl acetate and methanol mixtures. The title compound was obtained as an almost colourless gum $^1$HNMR (60 MH$_z$) (CH$_3$OD) 4.6-3.6 (8H,complex) and 3.2 (9H,s) ppm.

2-[{2-(1-Imidazolecarbonyloxyethoxy)hydroxyphosphinyl}oxy]-N,N,N-trimethylethanaminium hydroxide, inner salt

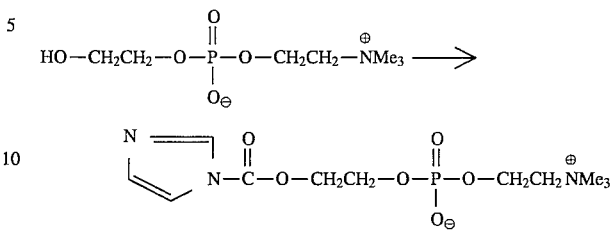

2-[{2-(Hydroxyethoxy)hydroxyphosphinyl}oxy]-N,N,N-trimethylethanaminiumhydroxide, inner salt (0.55 g, 2.4 mmol) was overlayered with dry dimethylsulphoxide (4 ml) and then treated with triethylamine (0.67 ml, 4.8 mmol) and then, portionwise, with 1,1'-carbonyldiimidazole (0.78 g, 4.8 mmol). The mixture was stirred at ambient temperature for 1 hour and was then dripped into dry, vigorously stirred acetone (150 ml). After 1 hour the colourless solid was collected by filtration, washed with acetone and dried in vacuo I.R. vmax (Nujol) 1763

$^1$HNMR (200 MH$_z$)(D$_2$O) δ 8.38 (1H,s), 7.66 (1H,s), 7.11 (1H,s), 4.69 (2H,m), 4.31 (4H,m), 3.61 (2H,m) and 3.2 (9H,s) ppm.

M.S. (FAB +ve ion—m-nitrobenzyl alcohol matrix) 322 (M+H), 228

EXAMPLE 3

2-[{4-(1-Imidazolecarbonyloxybutoxy)hydroxyphosphinyl}oxy]-N,N,N-trimethylethanaminium hydroxide, inner salt The title compound was prepared in a manner analogous to that described in Example 2 starting from 1,4-butanediol. Thus, in the same sequence of reactions 1,4-butanediol was converted into 2-[{4-(hydroxybutoxy)hydroxyphosphinyl}oxy]-N,N,N,-trimethylethanaminium hydroxide, inner salt (which has $^1$HNMR (60 MH$_z$)CD$_3$OD) 4.4 - 3.4 (8H, complex), 3.15 (9H,s) and 1.9 - 1.3 (4H, complex) ppm.M.S. (FAB +ve ion in m-nitrobenzyl alcohol) 256 (MH$^O$), 184) which was treated with 1,1'-carbonyldiimidazole, as described above, to give 2-[{4-(1-imidazolecarbonyloxybutoxy)hydroxyphosphinyl}oxy]-N,N,N-trimethylethanaminium hydroxide, inner salt $^1$HNMR (200 MH$_z$) (D$_2$O) δ 8.32 (1H,s) 7.61 (1H,s), 7.01 (1H,s), 4.51 (2H,t), 4.31 (2H,m), 4.00 (2H,q), 3.69 (2H,m) 3.23 (9H,s) and 2.0-1.7 (4H,m) ppm MS (FAB, +ve ion m-nitrobenzyl alcohol) 350 (MH$^O$), 238, 166

EXAMPLE 4

1,2-bis-$^O$-Imidazolecarbonyl-sn-glycero-3-phosphoryl choline

The title compound was obtained in an analogous manner as that described above from the reaction of glycerophosphorylcholine cadmium chloride complex with 1,1'-carbonyldiimidazole in dimethyl sulphoxide. The compound was isolated by precipitation of the reaction mixture from ethyl acetate. The compound has $^1$HNMR (60 MH$_z$) D$_2$O 8.3 (2H,m), 8.55 (2H,m), 7.0 (2H,s), 4.9-4.4 (2H,m), 4.4-3.9 (5H, complex), 3.55 (2H,m) and 3.1 (9H,s) ppm.

EXAMPLE 5: Contact Lens Treatment

A number of cross-linked 4-hydroxyethylmethacrylate-co-methacrylic acid copolymer contact lenses were treated with 2-[(2-(1-imidazolecarbonyloxyethoxy)hydroxyphosphinyl)oxy]-N,N,N-trimethylethanaminiumhydroxide, inner salt.

The lenses were first washed in sodium bicarbonate buffer at pH 9.0 for 1 hour (10 ml/lens). They were then rolled in sample vials on a Denley Spiramix 5 roller mixer in sodium bicarbonate buffered 2-[(2-(1-imidazolecarbonyloxyethoxy)hydroxyphosphinyl)oxy]-N,N,N-trimethylethanaminium hydroxide, inner salt solution (160 mg/ml) (1.04 ml/lens) for 16 hours. The lenses were then washed in borate buffered saline (pH 7.1) for 5 hours (20 ml/lens). The buffer was replaced every hour with fresh solution, finally the lenses were re-equilibrated and stored in borate buffered saline at pH 7.1 (1.7 ml/lens).

The lenses were tested for the level of protein deposition by a spectrophotometric method and their equilibrium water content measured by both gravimetric and refractive index techniques. These tests were carried out on the lenses before and after sterilization by conventional autoclaving (121° C. for 20 minutes).

Protein deposition studies were carried out as follows:

The treated lenses were each immersed in a know volume of a protein solution comprising a known concentration of both bovine serum albumin and chicken egg lysozyme. The solutions were then incubated at 34° C. for 24 hours. The lenses were then rinsed with borate buffered saline, clamped in holders and immersed in borate buffered saline in quartz UV spectrophotometer cells. The level of protein on the lens was determined by comparing the absorption at 280 nm of the untreated lens with that of the treated. Through the used of a calibration curve it was possible to calculate the mass of protein adsorbed per unit area of lens and the reduction in protein deposition relative to the untreated lens.

The equilibrium water content of the lenses was measured gravimetrically. Treated and untreated lenses were removed from borate buffered saline, lightly blotted to remove surface moisture and then weighed. The lenses were then dried under vacuum at 80° C. for 24 hours and reweighed. The equilibrium water content was calculated as a percentage by subtracting the dry weight from the wet weight, dividing this by the wet weight and multiplying by 100.

Lenses treated by this process displayed a reduction in protein deposition of 96% compared to an untreated lens.

|  | Protein | | Equilibrium Water |
|---|---|---|---|
|  | $\mu g cm^{-2}$ | % Reduction | Content (%) |
| Treated | 64 | 96 | 70 |
| Untreated | 1600 | 0 | 70 |

EXAMPLE 6

Diagnostic Device Surface Treatment

The components of a diagnostic device were treated initially in a plasma barrel etcher with 2-methyl-2-propanol to provide a polymeric surface with hydroxyl functional groups. This modified surface was treated with 2-[(2-(1-Imidazolecarbonyloxyethoxy)hydroxyphosphinyl)oxy]-N,N,N-trimethylethanaminium hydroxide, inner salt.

The components were first washed in sodium bicarbonate buffer at pH 9.0 and then soaked in a solution of the 2-[(2-(1-Imidazolecarbonyloxyethoxy)hydroxyphosphinyl)oxy]-N,N,N-trimethylethanaminium hydroxide, inner salt (50 mg/ml) in sodium bicarbonate buffer for 1 hour. The components were removed and washed in distilled water.

The components were examined for platelet activation by scanning electron microscopy. Treated surfaces showed no platelet activation.

We claim:

1. A process for preparing a compound of formula (IV)

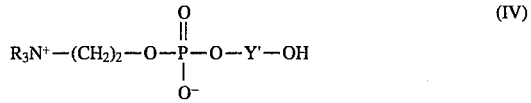

in which the groups R may be the same or different and each is a straight or branched $C_{1-4}$ alkyl group, and Y' is $-(CH_2)_p-$ or $-(CH_2)_a-Ar-(CH_2)_b-$, where p is from 1 to 30; Ar is a para- or meta-disubstituted aryl or heteroaryl group; and a and b are the same or different and each is from 0 to 5 and a+b is from 1 to 10;

which process comprises monoprotecting a diol of formula:

$$HO-Y'-OH$$

in which Y' is as hereinbefore defined; coupling the protected diol with 2-chloro-2-oxo-1,3,2- dioxaphospholane in the presence of an inorganic or organic base; reacting the coupled product with an anhydrous tertiary amine of formula $NR_3$ wherein the groups R are as hereinbefore defined and deprotecting the protected, hydroxy phosphorylcholine derivative thus obtained in a non-aqueous organic solvent to provide a compound of formula (IV).

2. A process according to claim 1 for preparing

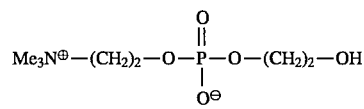

3. A process according to claim 1, wherein the non-aqueous organic solvent is a mixture of tetrahydrofuran and methanol.

4. A process according to claim 1, wherein the protected, hydroxy phosphorylcholine derivative is deprotected using hydrogen fluoride.

5. A process according to claim 4, wherein the hydrogen fluoride is a hydrogen fluoride pyridine complex.

6. A process according to claim 2, wherein the protected, hydroxy phosphorylcholine derivative is deprotected using hydrogen fluoride.

7. A process according to claim 6, wherein the hydrogen fluoride is a hydrogen fluoride: pyridine complex.

8. A process according to claim 1, wherein the diol is monoprotected using a silylating agent.

9. A process according to claim 8, wherein the diol is monoprotected using a silylating agent in the presence of an inert organic solvent.

10. A process according to claim 4, wherein the diol is monoprotected using a silylating agent.

* * * * *